United States Patent
Lyons

[11] 3,972,953
[45] Aug. 3, 1976

[54] GROUP VIII METAL COMPLEX CATALYZED HALOGEN EXCHANGE REACTION

[75] Inventor: James E. Lyons, Wallingford, Pa.

[73] Assignee: Sun Ventures, Inc., St. Davids, Pa.

[22] Filed: Jan. 22, 1975

[21] Appl. No.: 542,998

[52] U.S. Cl.......................... 260/651 R; 260/658 R; 260/653; 252/431 P; 252/472
[51] Int. Cl.²......................................... C07C 17/20
[58] Field of Search............ 260/658 R, 651 R, 653

[56] References Cited
UNITED STATES PATENTS

| | | | |
|---|---|---|---|
| 3,370,096 | 2/1968 | Donaldson et al. | 260/658 R |
| 3,804,870 | 4/1974 | Hughes et al. | 260/658 R |
| 3,857,900 | 12/1974 | Wilkinson | 260/658 R |

Primary Examiner—D. Horwitz
Attorney, Agent, or Firm—J. Edward Hess; Donald R. Johnson; Stanford M. Back

[57] ABSTRACT

Alkyl halide exchange may be catalyzed under mild conditions in homogeneous solution by ligand stabilized, low valent, coordinatively unsaturated $d^6$ or $d^8$ Group VIII metal complexes of the formula $$M^nX_nL_x$$

wherein M is a metal of Group VIII of the Periodic Table; X is chloride, bromide or iodide; $n$ is 1 or 2; L is a neutral ligand such as CO; trialkyl or triaryl-phosphines, arsines, amines, or stibines and the like; $x$ is an integer from 2–4 and $L_x$ represents $x$ neutral ligands which may be the same or different.

In this manner the halide group of one alkyl halide may be replaced by the halogen of another alkyl halide by a process of alkyl halide exchange.

9 Claims, No Drawings

GROUP VIII METAL COMPLEX CATALYZED HALOGEN EXCHANGE REACTION

BACKGROUND OF THE INVENTION

This invention relates to a catalytic process for the exchange of halide groups by alkyl halide exchange. More particularly this invention relates to the facile interconversion of alkyl halides under mild conditions in the presence of a ligand stabilized, low valent, coordinatively unsaturated $d^6$ or $d^8$ Group VIII metal complex in homogeneous solution to form different halohydrocarbons fromm those started with, and desirably mixed halohydrocarbons. By "mixed halohydrocarbons" is meant those hydrocarbons having more than one halogen group, each such group being different. This is the first example of this type of catalytic activity for this group of complexes.

SUMMARY OF THE INVENTION

In accordance with the present invention, it has now been found that two or more alkyl halides, RX, where X is chloride, bromide or iodide, will react to exchange their halogen moieties, X, in the presence of catalytic quantities of ligand stabilized, low valent, coordinatively unsaturated $d^6$ or $d^8$ Group VIII metal complexes in homogeneous solution. The metal complexes which are effective catalysts for this reaction have the formula:

$$M^nX_nL_x$$

wherein M is a metal of Group VIII of the periodic Table, preferably Ru, Rh, Ir, or Co; X is chloride, bromide or iodide; n is an integer which equals 1 or 2; L is a neutral ligand such as CO; trialkyl- or triaryl- phosphines, arsines, amines, or stibines, or the like and may be the same or different moieties; and x is an integer of from 2–4. The reaction is carried out at temperatures in the range of 20° to 180°C preferably 80° to 120°C and under enough pressure of an inert gas to keep all components in the liquid phase at this temperature. Pressure is desirably in the range of from 15 psi to 150 psi. The inert gas may be argon, nitrogen, CO or any other gas which does not interfere or react with the alkyl halides under the conditions of the reaction.

These reactions may be described by the following equations:

$$RX + R'X' \rightarrow RX' + R'X \quad (1)$$

$$RX' + R_2CX_2 \rightarrow RX + R_2CXX' \quad (2)$$

$$RX' + RCX_3 \rightarrow RX + RCX'X_2 \quad (3)$$

$$RX' + CX_4 \rightarrow RX + CX'X_3 \quad (4)$$

$$RX' + XCR_2(CR_2)_xCR_2X \rightarrow RX + X'CR_2(CR_2)_xCR_2X \quad (5)$$

wherein R and R' are lower alkyl groups of from 1 to 15 carbon atoms, wherein R and R' are different; and X and X' are different halogens selected from a group consisting of Cl, Br and I.

DESCRIPTION OF THE INVENTION

The starting materials comprise branched and linear lower alkyl halides having from 1 to 30 carbon atoms, as defined above. Examples of starting materials coming within the purview of this invention include: methyl iodide, methyl bromide, methyl chloride, ethyl iodide, ethyl bromide, ethyl chloride, propyl iodide, propyl chloride, benzyl iodide, benzyl bromide, benzyl chloride, dichloromethane, dibromomethane, diiodomethane, trichloromethane, tribromomethane, triiodomethane, carbon tetrachloride, carbon tetrabromide, carbon tetraiodide, α, α-dichlorotoluene, α, α-dibromotoluene, α, α-diiodotoluene, α, α, α-trichlorotoluene, α, α, α-tribromotoluene, α, α, α-triiodotoluene, trifluoromethyl chloride, trifluoromethyl iodide, trifluoromethylbromide, 1,1-dichloroethane, 1,1-diiodoethane, 1,1-dibromoethane, 1,2-dichloroethane, 1,2-dibromoethane, 1,2-diiodoethane and other compounds of similar structure.

Examples of halogen exchange reactions are the following:

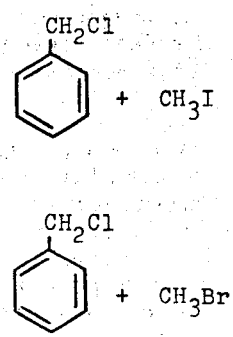

(6)

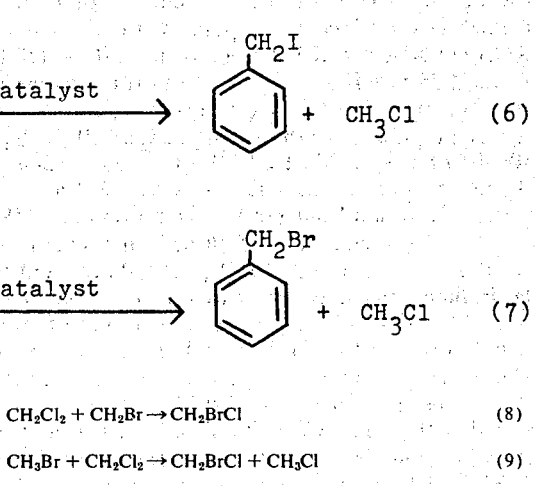

(7)

$$CH_2Cl_2 + CH_2Br_2 \rightarrow CH_2BrCl \quad (8)$$

$$CH_3Br + CH_2Cl_2 \rightarrow CH_2BrCl + CH_3Cl \quad (9)$$

$$\begin{array}{c}PhCH_2Cl\ + \\ BrCH_2CHBrCH_2Br \rightarrow ClCH_2CHBrCH_2Br\ + \\ PhCH_2Br\end{array} \quad (10)$$

$$CH_3Br + CF_3Cl \rightarrow CH_3Cl + CF_3Br \quad (11)$$

The reaction can be driven from left to right by using an excess of one of the reactants, depending upon the position of equilibrium of the particular reaction, which can readily be determined by those skilled in the art. Thus, the ratios of these starting materials are not critical, but can be easily optimized emperically. This reaction has utility in the production of valuable halogenated products from readily available halohydrocarbons. Mixed halohydrocarbons are articles of commerce having a variety of commercial applications. For example, in addition to the well known Freon mixed halomethanes (cf. Eq. 11) bromochloromethane (cf. Eqs. 8, 9) is manufactured for use as a fire extinguisher where it offers particular advantages for use in aircraft and portable extinguishers; and dibromochloropropane (cf. Eq. 10) is used alone or in formulations as a soil fumigant for control of nematodes and root diseases. The usual manner of preparation of these compounds is by the stiochrometric reaction of a halogenated hydrocarbon with some reagent to add or insert the second halogen component. A catalytic route to these materials offers an alternative and advantageous synthetic method. The examples in Eq. 6 and Eq. 7 illustrate a means of obtaining less available benzyl iodide and benzylbromide from the less costly benzyl chloride. In addition to the mixed halomethanes listed above, new mixed halomethanes heretofore unavailable become easy to prepare. Because of the difference in reactivity between the different carbon-halogen bonds, mixed halomethanes will be valuable intermediates in chemical synthesis in preparing compounds having the utilities enumerated above.

The catalyst of this process, as mentioned above, is a low valent, coordinatively unsaturated $d^6$ or $d^8$ Group VIII metal complex of the formula $$M^nX_nL_x$$

wherein M is a metal of Group VIII of the Periodic Table, and preferably Rh, Ir, Ru, Os or Co; X is chloride, bromide or iodide; n is 1 or 2; L is a neutral ligand such as CO, trialkyl- or triaryl- or mixed alkylaryl -phosphines, -arsines, -amines or -stibines, and the like; x is an integer of from 2 to 4; and $L_x$ represents x neutral ligands which may be the same or different. Included amongst these compounds are the catalysts: $RuCl_2(PPh_3)_3$, $RuCl_2(CO)(Ph_3P)_2$, $RuBr_2(PPh_3)_3$, $RuCl_2(PPh_2CH_3)_3$ and similar ruthenium complexes (see Hallman et al., J. Chem. Soc. (A), 3143 (1968), for the preparation of these compounds); $RhCl(Ph_3P)_3$, $RhCl(PPh_2CH_3)_3$, $RhCl(CO)(Ph_3P)_2$, and similar rhodium compounds (see Valarino, et al., J. Chem. Soc. (1957) 2287 and Young et al. Chem Commun. (1965) 131 for the preparation of these compounds); $IrCl(CO)(Ph_3P)_2$, $IrBr(CO)(Ph_3P)_2$, $IrCl(Ph_3P)_3$ and similar iridium complexes (see Vaska et al., J. Am. Chem. Soc. 87, 4970 (1962) for the preparation of iridium complexes); $[OsBr_2(Ph_3P)_3]_2$ and similar osmium complexes (see J. Chatt et al., J. Chem. Soc. (1961) 896 for their preparation); $CoBr(CO)_2(Ph_3P)_2$, $[Co(CO)_2Ph_3P)_2]^+PF_6^-$, $Co(CO)_2(Ph_3P)_2]^+BF_4^-$, and similar cobalt complexes (see Bressan et al, Inorg. Chem. 9, 1733, (1969) for the preparation of $CoBr(CO)_2(Ph_3P)_2$). $[Co(CO)_2(Ph_3P)_2]^+PF_6^-$ and $[Co(CO)_2(Ph_3P)_2]^+BF_4$ may be prepared by the addition of $AgPF_6$ or $AgBF_4$ to $CoBr(CO)_2(Ph_3P)_2$ according to Eq. 12 and Eq. 13, respectively:

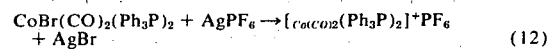
(12)

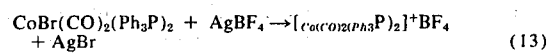
(13)

The process may readily be carried out by contacting the two halohydrocarbons to be exchanged with the catalyst at temperatures of 20° to 180°C and preferably from 80° to 120°C for a period of from 1 to 50 hours, depending upon the reactants, at external pressure of inert gas of from 15 to 250 psi and preferably 100 to 150 psi. An inert solvent such as benzene or toluene may be used, or an excess of one halohydrocarbon may be used as a solvent. The amount of catalyst employed should be about $10^{-1}$ to $10^{-5}$ mole per mole of starting material and preferably $10^{-2}$ to $10^{-4}$ mole. The products are recovered by distillation, crystallization or other conventional methods.

The invention will now be illustrated by the following examples.

EXAMPLE 1

The reaction illustrated in the general equation (1) was carried out using α-chlorotoluene and methyl iodide as reactants. Methyl iodide, 0.5 ml, and α-chlorotoluene, 5.0 ml, were stirred at 100°C under 150 psi of argon in the presence of 0.10 grams of $RhCl(CO)(Ph_3P)_2$. After 2.0 hours a 10% yield of α-iodotoluene was produced. Analyses were carried out by gc and products were isolated by preparative gc and identified by comparison of ir, nmt and mass spectra with authentic samples.

EXAMPLE 2

A series of runs illustrated in the general equation (2) was carried out using a large number of mixtures of halohydrocarbons. A 2 × $10^{-2}$ molar solution of the metal complex in a mixture of 5.0 ml $R_2CX_2$ and 0.5 ml RX (as defined in the table below) was stirred at 100°C under 150 psi of either argon or CO for the designated time. Product analysis was carried out by gc and products were isolated by preparative gc and identified by comparison of ms, ir and nmr spectra with authentic samples. Table I lists 19 examples of this reaction which demonstrate the scope and general applicability of the alkylhalide exchange reactions using several metal complexes and a variety of halohydrocarbon mixtures.

TABLE I

| ALKYL HALIDE EXCHANGE CATALYZED BY GROUP VIII METAL COMPLEXES | | | | | | | |
|---|---|---|---|---|---|---|---|
| REACTANTS | | | REACTION | | PRODUCTS | | % |
| RX' | $R_2CX'_2$ | CATALYST | TIME, Hrs. | GAS | RX | $R_2CXX'$ | EXCHANGE |
| $CH_3I$ | $CH_2Cl_2$ | none | 2.0 | Ar | — | — | none |
| $CH_3I$ | $CH_2Cl_2$ | $IrCl(CO)(Ph_3P)_2$ | 2.0 | Ar | $CH_3Cl$ | $CH_2ICl$ | 25 |
| $CH_3I$ | $CH_2Cl_2$ | $[Co(CO_2(Ph_3P)_2^+PF_6^-$ | 2.0 | CO | $CH_3Cl$ | $CH_2ICl$ | 70 |
| $CH_3I$ | $CH_2Cl_2$ | $RuCl_2(Ph_3P)_3$ | 2.0 | Ar | $CH_3Cl$ | $CH_2ICl$ | 98 |
| $CH_3I$ | $CH_2Cl_2$ | $RhCl(Ph_3P)_3$ | 2.0 | Ar | $CH_3Cl$ | $CH_2ICl$ | 98 |
| $CH_3I$ | $CH_2Cl_2$ | $RhCl(Ph_3P)_3$ | 2.0 | CO | $CH_3Cl$ | $CH_2ICl$ | 97 |
| $CH_3I$ | $CH_2Cl_2$ | $RhCl(CO)(Ph_3P)_2$ | 2.0 | Ar | $CH_3Cl$ | $CH_2ICl$ | 96 |
| $CH_3I$ | $CH_2Cl_2$ | $RhCl(CO)Ph_3P)_2$ | 2.0 | CO | $CH_3Cl$ | $CH_2OICl$ | 96 |
| $CH_3I$ | $CH_2Br_2$ | $RhCl(CO)(Ph_3P)_2$ | 2.0 | Ar | $CH_3Br$ | $CH_2IBr$ | 93 |
| $CH_3I$ | $CH_2Br_2$ | $RhCl(CO)(Ph_3P)_2$ | 2.0 | CO | $CH_3Br$ | $CH_2IBr$ | 95 |
| $CH_3I$ | $PhCHBr_2$ | $RhCl(CO)(Ph_3P)_2$ | 2.5 | CO | $CH_3Br$ | $CH_2IBr$ | 94 |
| $CH_3I$ | $PhCHCl_2$ | $RhCl(CO)(Ph_3P)_2$ | 2.0 | CO | $CH_3Cl$ | $PhCHICl$ | <10 |
| $CH_3CH_2I$ | $CH_2Cl_2$ | $RhCl(CO)(Ph_3P)_2$ | 2.0 | CO | $CH_3CH_2Cl$ | $CH_2ICl$ | 17 |
| $(CH_3)_2CHI$ | $CH_2Cl_2$ | $RhCl(CO)(Ph_3P)_2$ | 18.0 | CO | — | — | NR |
| $PhCH_2Br$ | $CH_2Cl_2$ | $RhCl(CO)(Ph_3P)_2$ | 2.0 | CO | $PhCH_2Cl$ | $CH_2BrCl$ | 10 |

TABLE I-continued
ALKYL HALIDE EXCHANGE CATALYZED BY GROUP VIII METAL COMPLEXES

| REACTANTS | | | REACTION | | PRODUCTS | | % |
|---|---|---|---|---|---|---|---|
| RX' | $R_2CX'_2$ | CATALYST | TIME, Hrs. | GAS | RX | $R_2CXX'$ | EXCHANGE |
| $PhCH_2Br$ | $CH_2Cl_2$ | $RhCl(CO)(Ph_3P)_2$ | 22.5 | CO | $PhCH_2Cl$ | $CH_2BrCl$ | 71 |
| $PhCH_2Br$ | $CH_2Cl_2$ | $RhCl(CO)(Ph_3P)_2$ | 2.0 | Ar | $PhCH_2Cl$ | $CH_2BrCl$ | 8 |
| $CH_3Br$ | $CH_2Cl_2$ | $RhCl(CO)(Ph_3P)_2$ | | CO | $PhCH_2Cl$ | $CH_2BrCl$ | 13 |
| $CH_3CH_2Br$ | $CH_2Cl_2$ | $RhCl(CO)(Ph_3P)_2$ | 21.0 | CO | $CH_3CH_2Cl$ | $CH_2BrCl$ | 0.5 |

EXAMPLE 3

In accordance with the procedure of Example 1, iododichloromethane is formed from methyl iodide and chloroform; iodotrichloromethane is formed from methyl iodide and carbon tetrachloride; and 1-chloro-2,3-dibromopropane is formed from methyl bromide and 1,2,3-tribromopropane in good yield.

EXAMPLE 4

A $2 \times 10^{-2}$ M solution of $RhCl(CO)(Ph_3P)_2$ in dichloromethane, 2.5 ml and dibromomethane 2.5 ml was stirred at 100°C under 150 psi CO for 2.0 hrs. After this time a 10% yield of chlorobromomethane was formed as the sole reaction product.

EXAMPLE 5

In accordance with the procedures of Example 2, a $2 \times 10^{-2}$ M solution of metal complex in 0.5 ml iodomethane and 5.0 ml methylenechloride is stirred at 100°C under 150 psi of inert gas for 2.0 hours. Appreciable exchange is observed when the metal complex is $RuCl_2(PPh_2CH_3)_3$, $RhCl(PPh_2CH_3)_3$, $RhCl(CO)[(n-C_3H_7)_3P]_2$, $IrBr(CO)Ph_3P)_2$, $IrCl(Ph_3P)_3$, $[OsBr_2(Ph_3P)_3]_2$ or $[Co(CO)_2(Ph_3P)_2]^+BF_4^-$. Reactions are run under both CO and Ar.

The invention claimed is:

1. A process for the exchange of halogen moieties between two or more lower alkyl halides or aryl-substituted alkyl halides to form corresponding halophydrocarbons having different halogen moieties, or mixed halohydrocarbons, or both, which comprises contacting at least two such alkyl halides, where the halogen moieties on each differ from each other, in the liquid phase, in the presence of a low valent, coordinatively unsaturated $d^6$ or $d^8$ Group VIII metal complex catalyst of the formula

$M^nX_nL_x$ wherein M is ruthenium, rhodium osmium, iridium or cobalt; X is chloride, bromide, or iodide; L is a neutral ligand selected from the group consisting of CO; and trialkyl- or triaryl- or mixed alkylaryl-phosphines; $n$ is 1 or 2; $x$ is an integer of from 2 to 4; and wherein said neutral ligands may be the same or different.

2. The process according to claim 1 wherein the reaction is carried out under pressure.

3. The process according to claim 2 wherein the pressure is in the range of from about 15 to 250 psi.

4. The process according to claim 1 wherein the reaction is carried out at a temperature of from about 20° to 180°C.

5. The process according to claim 1 wherein the amount of catalyst employed is from about $10^{-1}$ to $10^{-5}$ mole per mole of starting material.

6. The process according to claim 1 wherein the alkylhalide is a lower alkyl halide having from 1 to 30 carbon atoms, or an aryl- substituted lower alkyl halide, or mixtures thereof.

7. The process according to claim 1 wherein the catalyst is $RhCl(CO)(Ph^3P)_2$, $IrCl(CO)(Ph_3P)_2$, $[Co(CO)_2(Ph_3P)_2]^+PF_6^-$, $RuCl_2(PPh_3)_3$, or $RhCl(Ph_3P)_3$, $RuCl_2(PPh_2CH_3)_3$, $RhCl(PPh_2CH_3)_3$, $RhCl(CO)[(n-C_3H_7)_3P]_2$, $TrBr(CO)(Ph_3P)_2$, $IrCl(Ph_3P)_3$, $[OsBr_2(Ph_3P)_3]_2$, $[Co(CO)_2(Ph_3P)_2]^+BF_4^-RuCl_2(CO)(Ph_3P)_2$, $RuBr_2(PPh_3)_3$, $CoBr(CO)_2(Ph_3P)_2$.

8. The process according to claim 1 wherein the reaction is carried out in the presence of an inert solvent.

9. The process according to claim 1 wherein the reaction is carried out in the presence of a substantial excess of one of the alkyl halide reactants.

* * * * *